(12) United States Patent
Costantino et al.

(10) Patent No.: US 7,868,194 B2
(45) Date of Patent: Jan. 11, 2011

(54) PROCESS FOR THE PREPARATION OF 21-HYDROXY STEROIDS WITH CONTROL OF THE EPIMERIC DISTRIBUTION AT THE C-21 POSITION

(75) Inventors: Francesca Costantino, Milan (IT); Roberto Lenna, S. Giorgio Su Legnano (IT); Maria Julieta Comin, Buenos Aires (AR); Javier Ramirez, Buenos Aires (AR); Juan Bautista Rodriguez, Buenos Aires (AR)

(73) Assignee: Industriale Chimica S.R.L., Milan (IT)

( * ) Notice: Subject to any disclaimer, the term of this patent is extended or adjusted under 35 U.S.C. 154(b) by 887 days.

(21) Appl. No.: 11/666,096

(22) PCT Filed: Oct. 20, 2005

(86) PCT No.: PCT/EP2005/055410

§ 371 (c)(1),
(2), (4) Date: Apr. 23, 2007

(87) PCT Pub. No.: WO2006/045745

PCT Pub. Date: May 4, 2006

(65) Prior Publication Data

US 2008/0114180 A1    May 15, 2008

(30) Foreign Application Priority Data

Oct. 21, 2004    (IT)    ................. MI2004A002001

(51) Int. Cl.
*C07J 9/00*    (2006.01)
(52) U.S. Cl. ...................................... 552/555
(58) Field of Classification Search .................. 552/555
See application file for complete search history.

(56) References Cited

FOREIGN PATENT DOCUMENTS

| EP | 0 007 823 | 2/1980 |
|---|---|---|
| EP | 0 574 317 | 10/1996 |
| EP | 0 581 649 | 10/1998 |
| FR | 2 149 302 | 3/1973 |

OTHER PUBLICATIONS

PCT Written Opinion for PCT/EP2005/055410. "Chemistry of Oxaziridines, Asymmetric Oxidation of Ketone Enolates Using Enantiomerically Pure (Camphorsulfonyl) Oxaziridine," Franklin Davis et al., J.Am Chem. Society, 1990, 112, pp. 6679-6690.

"Cerium(III) Chloride, a Novel Reagent for Nonaqueous Selective Conversion of Dioxolanes to Carbonyl Compounds," Marcantini et al., J. Org. Chem., 1997, 62, pp. 4183-4184.

*Primary Examiner*—Barbara P Badio
(74) *Attorney, Agent, or Firm*—Reising Ethington P.C.

(57) ABSTRACT

A process is described for preparing, exclusively by chemical way, 21-hydroxy steroids having progestinic activity, said process having a high stereochemical control at C-21 position.

27 Claims, No Drawings

PROCESS FOR THE PREPARATION OF 21-HYDROXY STEROIDS WITH CONTROL OF THE EPIMERIC DISTRIBUTION AT THE C-21 POSITION

The patent application is based on a priority patent application PCT/EP2005/055410, filed 20 Oct. 2005, which in turn, is based on Italian patent application MI2004A002001, filed 21 Oct. 2004, both of which are hereby incorporated by reference.

FIELD OF THE INVENTION

The present invention refers to the field of processes for preparing steroids, and in particular to a new process for preparing, by exclusively chemical way, 21(S)-hydroxy-4,9-gonadien-3,20-diones, synthetic progestinic steroids, having general formula (I):

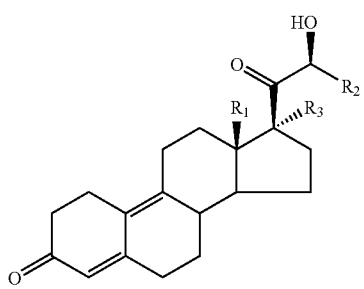

wherein $R_1$ is an alkyl group having from 1 to 3 carbon atoms, $R_2$ is an alkyl group having from 1 to 12 carbon atoms, $R_3$ is an alkyl group having from 1 to 4 carbon atoms.

In particular, the compound with formula (I) in which $R_1$, $R_2$ and $R_3$ are methyl groups, known with the common name trimegestone, is used as an oral contraceptive and, alone or in combination con estradiol, in postmenopause hormone replacement therapy.

STATE OF THE ART

Various processes are known for preparing trimegestone and 21-hydroxy steroid analogues.

For example, in the European Patent Application No. 0007823 a process is described for preparing 21-hydroxy steroids with formula (I) starting from corresponding 3,3-alkylendioxy-5(10),9(11)-gonadien-20-ones, which in their turn were prepared as described in the French Patent No. 2 149 302. In EP 0007823 a detailed example of the preparation of trimegestone is given, from which it emerges that that product is obtained in the form of an epimeric mixture, containing almost the same quantity of the two epimers 21(S) and 21(R), in which the hydroxyl at the C-21 position is respectively in position S or R.

Since the desired product is the epimer 21(S), the process described in EP 0007823 requires a final purification, with a waste of about 50% of the reaction product, and this has weighed heavily on the process economy. Moreover, to eliminate the undesired epimer from the final product, chromatography is used but, as the quantity of epimer to be eliminated is practically the same as the quantity of desired epimer, the separation is not satisfactory.

In the literature, other processes are described for obtaining 21-hydroxy steroids of formula (I), for example the processes described in the European Patents No. 0 581 649 and No. 0 574 317.

In EP 0 574 317, to obtain the desired diastereoselection in position 21, microbiological reactions are used which, though using micro organisms that are not difficult to grow, require different systems, technology and professional skills from those of industrial companies that operate only by chemical synthesis.

Instead the process described in EP 0 581 649, to obtain the desired diastereoselection in position 21, contemplates the use of enzymes which allow a first reaction yield of 50%. To recover the product, a series of chemical reactions on the undesired epimer is then necessary, obtaining however an epimeric purity lower than 95%.

From the above it is therefore clear that the need is still felt to have a process for preparing 21(S)-hydroxy steroids by an exclusively chemical way.

SUMMARY OF THE INVENTION

Now the Applicant has developed a process which, proceeding in an exclusively chemical way, allows high yields of 21(S)-hydroxy steroids of general formula (I) as defined above to be obtained with a high control of stereochemistry, thus overcoming the disadvantages illustrated above for the known processes.

Subject of the present invention is therefore a process for preparing 21(S)-hydroxy steroids with epimeric purity higher than 50%, having general formula (I)

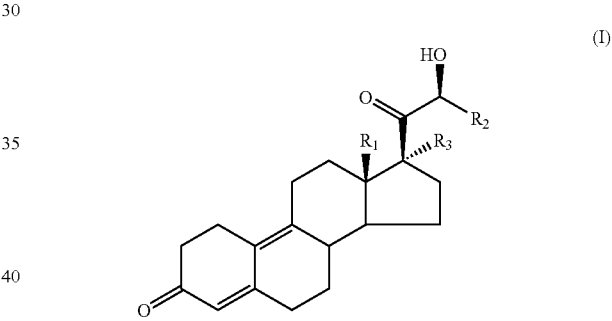

wherein $R_1$ is an alkyl group having from 1 to 3 carbon atoms, $R_2$ is an alkyl group having from 1 to 12 carbon atoms, $R_3$ is an alkyl group having from 1 to 4 carbon atoms, comprising the following steps:

i) reaction of 3,3-alkylendioxy-17β-(1-oxoalkyl)-5(10),9(11)-gonadiene of formula (II) with an oxaziridine in the presence of a strong organic base in an organic solvent, to give 3,3-alkylendioxy-17β-[(2S)-2-hydroxy-1-oxoalkyl]-5(10),9(11)-gonadiene of general formula (III)

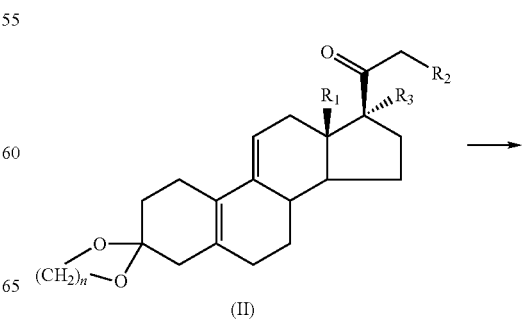

-continued

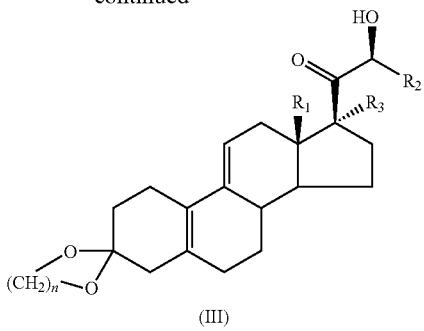

(III)

wherein $R_1$, $R_2$ and $R_3$ are defined as above, and n is an integer ranging from 2 to 4, ii) reaction of 3,3-alkylendioxy-17β-[(2S)-2-hydroxy-1-oxoalkyl]-5(10),9(11)-gonadiene of general formula (III) with a Cerium compound in an organic solvent, to obtain the desired 21(S)-hydroxy steroids of general formula (I)

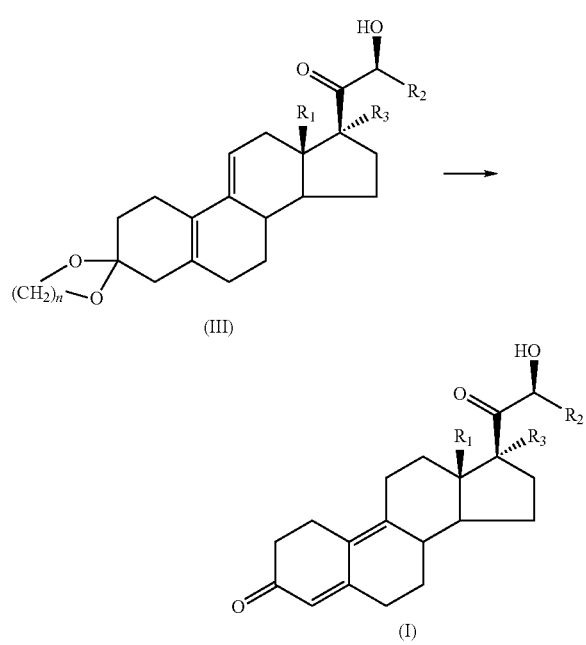

wherein $R_1$, $R_2$ and $R_3$ are defined as above, and n is an integer ranging from 2 to 4.

Characteristics and advantages of the invention will be illustrated in detail in the following description.

DETAILED DESCRIPTION OF THE INVENTION

The process of the invention allows the preparation, by an exclusively chemical way, of 21(S)-hydroxy steroids of general formula (I) with an epimeric purity higher than 50%, and preferably with a purity higher than 95%.

An increase of the epimeric purity up to more than 99.5% may be obtained by subjecting the 21(S)-hydroxy steroids coming from step ii) to gel chromatography with an organic solvent as eluent.

The reaction in step i) of the process of the invention is carried out starting from the compound of general formula (II), in an organic solvent which is typically tetrahydrofurane, also with the addition of a solvent selected from the group consisting of toluene, dimethoxyethane and ethyl ether, and at a temperature between −90 and −30° C.

According to a particularly preferred embodiment of the invention, the reaction in step i) of the process is carried out in pure tetrahydrofurane, and at a temperature between −80 and −70° C.

The starting compounds of the present process having general formula (II) are known compounds, and they may be prepared for example as described in the French Patent No. 2,149,302.

Compounds preferably used as starting compounds in the present process are the compounds of general formula (II) listed above in which n is 2.

The oxaziridine used as reagent in step i) of the present process is for example a resolved chiral oxaziridine, preferably selected from among trans-2-(phenylsulphonyl)-3-phenyloxaziridine, (1S)-(+)-(10-camphorylsulphonyl) oxaziridine and 1R-(−)-(10-camphorylsulphonyl) oxaziridine.

These chiral reagents are available on the market, as in the case of 1R-(−)-(10-camphorylsulphonyl)oxaziridine, or they may be easily prepared with methods known by any skilled in the art. Example 1 below shows an example of the preparation of trans-2-(phenylsulphonyl)-3-phenyloxaziridine.

Excellent results in terms of epimeric purity of the desired product were obtained using 1R-(−)-(10-camphorylsulphonyl)oxaziridine.

The reaction of the compounds of formula (II) with an oxaziridine in step ii) must be carried out in the presence of a strong organic base, selected for example from the group consisting of lithium diisopropylamide, n-butyl lithium, methyl lithium, n-hexyl lithium, sodium bis(trimethylsylil) amide, lithium bis(trimethylsylil)amide, potassium hexamethyl disilazane, hexamethyl disilazane, potassium tert-butylate, and mixtures thereof. Preferably, the organic base is potassium hexamethyl disilazane or mixtures of hexamethyl disilazane and potassium tert-butylate.

The hydrolysis of the alkylendioxy group in position 3 to reconstitute the 3-keto group, and the isomerisation of the 5(10),9(11)-diene system into the 4,9-diene is carried out in step ii) by reaction of the intermediate of general formula (III) with a Cerium compound, preferably a halogenated derivative thereof, and more preferably with Cerium chloride heptahydrate.

The reaction temperature in step ii) ranges, for example, between 20 and 120° C. According to a preferred embodiment of the process of invention, the reaction in step ii) is carried out in the presence of a sodium or potassium halide, and preferably in the presence of sodium iodide.

The organic solvent used in step ii) may be a solvent that can be mixed with water, possibly added with water in a maximum percentage of 10% by volume with respect of the total volume of the solvent itself. Preferably the organic solvent used for the reaction in step ii) is acetonitrile.

When the 21(S)-hydroxy steroids coming from step ii) are subjected to gel chromatography, the gel used as the stationary phase may be selected for example from the group consisting of silica gel, florisil, sephadex, neutral alumina, acidic alumina, and basic alumina. Preferably the stationary phase consists of silica gel having granulometry between 5 and 200 μm.

The organic solvent used as eluent may instead be selected, for example, from the group consisting of ethyl ether, isopropyl ether, ethylacetate, isopropyl acetate, methylene chloride, acetone, tetrahydrofurane, methanol, ethanol, isopropanol, hexane (n-hexane or a mixture of isomers), heptane (n-heptane or a mixture of isomers), toluene, and mixtures thereof; and preferably the eluent is a toluene/ethyl acetate or methylene chloride/ethyl acetate gradient.

According to a preferred embodiment of the present process, the preparation of the chromatographic column and the elution take place at a temperature between 0 and 50° C., and a pressure between 0 and 2000 psi.

The 21(S)-hydroxy steroids of general formula (I) obtained after gel chromatography may also be subjected to crystallisation with a solvent, in which the crystallisation solvent is selected for example from the group consisting of ethyl ether, isopropyl ether, ethyl acetate, isopropyl acetate, methyl acetate, dimethoxyethane, methanol, ethanol, isopropanol, methylene chloride, acetone, dimethylacetamide, dimethylformamide, and mixtures thereof. Preferably, the crystallisation solvent is ethyl ether.

The present process, as described above, applies preferably to the preparation of 21(S)-hydroxy steroids of general formula (I) in which $R_1$, $R_2$ and $R_3$ are methyl groups, i.e. to the preparation of trimegestone.

The following examples are given for illustrative purposes and do not limit the present invention.

Example 1

Preparation of (±)-trans-2-(phenylsulphonyl)-3-phenyloxaziridine

A 3 l round-bottom flask is filled with 150 g of 5° molecular sieves, 2 g of an ion exchange resin, such as AMBERLYST® 15 resin (Amberlyst® is a registered trademark owned by Rohm & Haas Company, Philadelphia, Pa.) 157 g of benzenesulphonamide, 1.65 l of toluene and 107.5 g of distilled benzaldehyde.

The mixture is refluxed under argon atmosphere, distilling the reaction water for about 16 hours, then cooled to 20° C., and the suspension is filtered washing the filtrate with toluene. The toluene phase is then concentrated with a rotary evaporator, obtaining an oil which solidifies when recovered with heptane.

The solid product, ground in pentane until a filterable powder is obtained, is filtered and dried, obtaining 210 g of N-benzylidene benzenesulphonamide.

The raw product thus obtained is refluxed in 150 ml of ethyl acetate and, when completely dissolved, it is cooled adding 400 ml of pentane.

It is kept under stirring at 20° C., obtaining the crystallisation of the sulphonimine in 3-4 hours.

The solid is filtered and dried under reduced pressure and at 20° C. to a constant weight, finally obtaining 188 g of product in the form of white crystals, which was subjected to mass spectrometry and NMR, proving to be N-benzylidene benzenesulphonamide.

$^1$H-NMR (300 MHz, CDCl$_3$): δ (ppm) 9.04 (1H, s); 8.00 (2H, d, J=8 Hz); 7.90 (2H, d, J=8 Hz); 7.60 (2H, q, J=7 Hz); 7.52 (2H, t, J=8 Hz); 7.46 (2H, t, J=8 Hz).

Electronic impact mass spectrometry: m/z [245]=M$^+$, [181], [157], [141], [104]

A multy-necked flask is filled with 500 ml of a saturated aqueous solution of NaHCO$_3$, 12.5 g of benzyltriethylammonium chloride and a solution obtained by dissolving 122 g of N-benzylidene benzenesulphonamide prepared as described above, in 380 ml of chloroform.

The mixture is cooled to 0/5° C. and 112 g of 85% m-chloroperbenzoic acid dissolved in 1 l of chloroform is added. It is stirred cold for 1 hour, then brought to a temperature of 20° C. and kept under stirring for 3 hours. The organic phase is separated and washed with water, then with water and sodium sulphite, and again with water. The organic phase is then anhydrified on potassium carbonate.

By filtration and concentration under reduced pressure and at a temperature lower than 40° C., a white solid is obtained which is then dissolved at 20° C. with 800 ml of ethyl acetate and the obtained solution is filtered.

400 ml of pentane are added to the filtered solution and it is cooled for 12 hours at 0/5° C., then filtered washing it with pentane.

The solid thus prepared is dried at 20° C. for 2 hours under reduced pressure, obtaining 80 g of the title product, which is kept at −18° C. away from the light.

$^1$H-NMR (300 MHz, CDCl$_3$): δ (ppm) 5.48 (1H, s); 7.36-7.48 (5H, m); 7.60-7.64 (2H, t, J=7 Hz); 7.72-7.76 (1H, t, J=7 Hz); 8.02-8.08 (2H, d, J=7 Hz).

Electronic impact mass spectrometry: m/z [261]=M$^+$, [245], [172], [157], [141], [125], [105].

Example 2

Preparation of 3,3-ethylendioxy-17β-[(2S)-2-hydroxy-1-oxopropyl]-17α-methylestra-5(10),9(11)-diene (compound of general formula (III) in which $R_1$, $R_2$, and $R_3$ are methyl groups, and n=2)

250 ml of anhydrous tetrahydrofurane are put into a multy-necked flask under Argon atmosphere and cooled to −78° C.

46 ml (27.5 mmole) of a solution of potassium hexamethyldisilazane (KHMDS) in tetrahydrofurane are added, and a solution prepared by dissolving 6.8 g of 3,3-ethylendioxy-17α-methyl-17β-(1-oxopropyl)estra-5(10),9(11))diene in 100 ml of tetrahydrofurane.

From the end of adding it is stirred for 30 minutes at −78° C., then 7.21 g of trans-2-(phenylsulphonyl)-3-phenyloxaziridine are added, prepared as described above in Example 1, dissolved in 100 ml of tetrahydrofurane.

From the end of adding it is stirred for 30 minutes at −78° C., then 100 ml of a saturated aqueous solution of NH$_4$Cl are added and the mixture is stirred, letting the temperature rise to 20° C.

The mixture is extracted with methylene chloride (500 ml×3); the organic phase is washed with water, dried on sodium sulphate, filtered and the solvent is eliminated under reduced pressure. 15 g of solid residue are obtained.

After column chromatography (silica gel, 200 g) eluting with ethyl acetate-hexane 9:1, 5.3 g of the compound of the title are obtained which according to NMR analysis is a mixture of epimers with ratio 21S:21 R of about 9:1.

$^1$H-NMR (300 MHz, CDCl$_3$): δ (ppm) 4.51-4.54 (H-21 R, m); 4.37-4.43 (H-21 S, m).

Example 3

Preparation of 17β-[(2S)-2-hydroxy-1-oxoproyl]-17α-methylestra-4(5),9(10)-dien-3-one (compound of general formula (I) in which $R_1$, $R_2$, and $R_3$ are methyl groups, commonly called "trimegestone")

In 750 ml of acetonitrile are dissolved 9 g of 3,3-ethylendioxy-17β-[(2S)-2-hydroxy-1-oxopropyl]-17α-methylestra-5(10),9(11)-diene in the form of an epimeric mixture prepared as described above in Example 2. To this solution are added 13.05 g of Cerium chloride heptahydrate and 650 mg of sodium iodide and the whole is refluxed for 3 hours.

The mixture is cooled to 20° C. and recovered with 1 l of a saturated aqueous solution of NaCl and with 1.5 l of ethyl acetate, then the phases are separated and the aqueous phase is extracted again with 1 l of ethyl acetate.

The united organic phases are then washed with HCl 1% (750 ml), with water-NaHCO$_3$ 5% (1.5 l), with water and a saturated solution of NaCl (500 ml) and finally with water (500 ml).

The organic solution is anhydrified on sodium sulphate, filtered, and the solvent is eliminated under reduced pressure. From the residue, chromatographed on silica gel (1 kg) eluting with the hexane—ethyl acetate mixture in a gradient from 9:1 to 4:1, are obtained, after drying under reduced pressure, 6.15 g of product. According to NMR analysis, the product is trimegestone with an epimeric ratio 21S:21 R of about 9:1.

$^1$H-NMR (300 MHz, CDCl$_3$): δ (ppm) 4.54-4.57 (H-21R, m); 4.39-4.45 (H-21S, m).

Example 4

Preparation of 3,3-ethylendioxy-17β-[(2S)-2-hydroxy-1-oxopropyl]-17α-methylestra-5(10),9(11)-diene (compound of general formula (III) in which R$_1$, R$_2$, and R$_3$ are methyl groups, and n=2)

250 ml of anhydrous tetrahydrofurane are put into a multy-necked flask under Argon atmosphere and cooled to −78° C.

80 ml of a solution of 8.08 g KHMDS in tetrahydrofurane are added and then a solution of 10 g of 3,3-ethylendioxy-17α-methyl-17β-(1-oxopropyl)estra-5(10),9(11)-diene in 150 ml of tetrahydrofurane.

From the end of adding it is stirred for 30 minutes at −78° C., then 9.3 g of (1R)-(−)-(10-camphorsulphonyl)oxaziridine (SIGMA-ALDRICH) dissolved in 150 ml of tetrahydrofurane are added. From the end of adding it is stirred for 30 minutes at −78° C.

150 ml of a saturated aqueous solution of NH$_4$Cl are added slowly, the mixture is stirred, letting the temperature rise to 20° C., then it is extracted with methylene chloride (600 ml×3). The organic phase is washed with water, dried on sodium sulphate, filtered and the solvent is eliminated under reduced pressure.

17.5 g of solid residue are obtained from which, after column chromatography (silica gel, 300 g) eluting with ethyl acetate-hexane 9:1, 9.4 g of 3,3-ethylendioxy-17α-methyl-17β-(2-hydroxy-1-oxopropyl)estra-5(10),9(11)-diene are obtained which according to NMR analysis is a mixture of epimers 21S and 21R, of which the epimeric ratio 21S/21R is between 31/1 and 35/1.

$^1$H-NMR (300 MHz, CDCl$_3$): δ (ppm) 5.58-5.62 (H-11, m, 1H); 4.54-4.57 (H-21R, m); 4.39-4.45 (H-21S, m, 1H); 4.0 (H-ethyleneketal, s, 4H); 3.02 (OH-21, d, J=9 Hz, 1H, the signal disappears by deuteration); 1.33 (CH$_3$-21, d, J=6 Hz, 3H); 1.18 (CH$_3$-17, s, 3H); 0.67 (CH$_3$-13, s, 3H).

Electronic impact mass spectrometry: m/z [386]=M$^+$, [358], [313], [285], [227].

Example 5

Preparation of 17β-[(2S)-2-hydroxy-1-oxopropyl]-17α-methylestra-4(5),9(10)-dien-3-one (compound of general formula (I) in which R$_1$, R$_2$, and R$_3$ are methyl groups, commonly called "TRIMEGESTONE")

9.4 g of 3,3-ethylendioxy-17α-methyl-17α-(2-hydroxy-1-oxopropyl)estra-5(10),9(11)diene prepared as describe above in Example 4 are dissolved in 800 ml of acetonitrile, 13.15 g of Cerium chloride heptahydrate and 675 mg of sodium iodide are added and the whole is refluxed for 3 hours.

The mixture is cooled to 20° C. and is recovered with 1 l of a saturated aqueous solution of NaCl and with 1.5 l of ethyl acetate.

The phases are separated and the aqueous phase is extracted again with 1 l of ethyl acetate.

The united organic phases are then washed with HCl 1% (750 ml), with water-NaHCO$_3$ 5% (1.5 l), with water and a saturated solution of NaCl (500 ml) and finally with water (500 ml).

The organic solution is anhydrified on sodium sulphate, filtered, and the solvent is eliminated under reduced pressure. The residue thus obtained is filtered on silica gel with the mixture of hexane and ethyl acetate obtaining, after drying under reduced pressure, 7.15 g of crude trimegestone with an epimeric ratio 21S/21R of about 31/1.

This epimeric mixture with ratio 21S/21R 31/1 was then further enriched in the epimer 21S by chromatography on silica gel, eluting with the toluene-ethyl acetate mixture in gradient and subsequent crystallisation with ethyl ether.

$^1$H-NMR (300 MHz, CDCl$_3$): δ (ppm) 5.70 (H-4, s, 1H); 4.41-4.48 (H-21, m, 1H); 2.97 (OH-21, d, J=10 Hz, 1H, the signal disappears by deuteration); 1.34 (CH$_3$-21, d, J=6.5 Hz, 3H); 1.19 (CH$_3$-17, s, 3H); 0.82 (CH$_3$-13, s, 3H).

Electronic impact mass spectrometry: m/z [342]=M$^+$, [297], [269], [227], [213], [199], [175], [161], [107].

[α]$_D$=−201 (CHCl$_3$, c=I)

P$_f$=118-120° C.

Example 6

Preparation of 3,3-ethylendioxy-17β-[(2S)-2-hydroxy-1-oxopropyl]-17α-methylestra-5(10),9(11)-diene (compound of general formula (III) in which R$_1$, R$_2$, and R$_3$ are methyl groups, and n=2)

250 ml of anhydrous tetrahydrofurane are put into a multi-necked flask under Argon atmosphere and cooled to −78° C.

80 ml of a solution of 8.08 g KHMDS in tetrahydrofurane are added and then a solution of 10 g of 3,3-ethylendioxy-17α-methyl-17β-(1-oxopropyl)estra-5(10),9(11)-diene in 150 ml of tetrahydrofurane.

From the end of adding it is stirred for 30 minutes at −78° C., then 9.3 g of (1S)-(+)-(10-camphorsulphonyl)oxaziridine (SIGMA-ALDRICH) dissolved in 150 ml of tetrahydrofurane are added.

From the end of adding it is stirred for 30 minutes at −78° C., then 150 ml of a saturated aqueous solution of NH$_4$Cl are added slowly and the mixture is stirred, letting the temperature rise to 20° C. It is extracted with methylene chloride (600 ml×3).

The organic phase is washed with water, dried on sodium sulphate, filtered and the solvent is eliminated under reduced pressure, finally obtaining 17.5 g of solid residue.

After column chromatography (silica gel, 300 g) eluting with ethyl acetate-hexane 9:1, 8.3 g of the compound in the title are obtained which according to NMR analysis is an epimeric mixture with a ratio 21S/21R of about 3.7/1.

Example 7

Preparation of 17β-[(2S)-2-hydroxy-1-oxopropyl]-17α-methylestra-4(5),9(10)-dien-3-one (compound of general formula (I) in which $R_1$, $R_2$, and $R_3$ are methyl groups, commonly called "TRIMEGESTONE")

Using 3,3-ethylendioxy-17α-methyl-17β-(2-hydroxy-1-oxopropyl)estra-5(10),9(11)-diene as described above in Example 6, and following the same procedure described above in Example 5, the product of the title was obtained.

The invention claimed is:

1. A process for the preparation of 21(S)-hydroxy steroids with epimeric purity higher than 50%, having general formula (I)

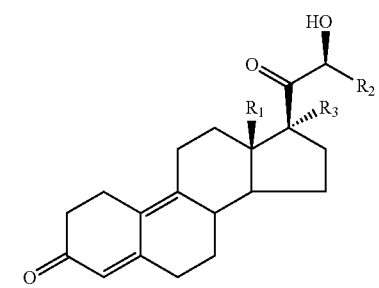

(I)

wherein $R_1$ is an alkyl group having from 1 to 3 carbon atoms, $R_2$ is an alkyl group having from 1 to 12 carbon atoms, $R_3$ is an alkyl group having from 1 to 4 carbon atoms, comprising the following steps i) reaction of 3,3-alkylendioxy-17β-(1-oxoalkyl)-5(10),9(11)-gonadiene of formula (II) with an oxaziridine in the presence of a strong organic base in an organic solvent, to give 3,3-alkylendioxy-17β-[(2S)-2-hydroxy-1-oxoalkyl]-5(10),9(11)-gonadiene of formula (III)

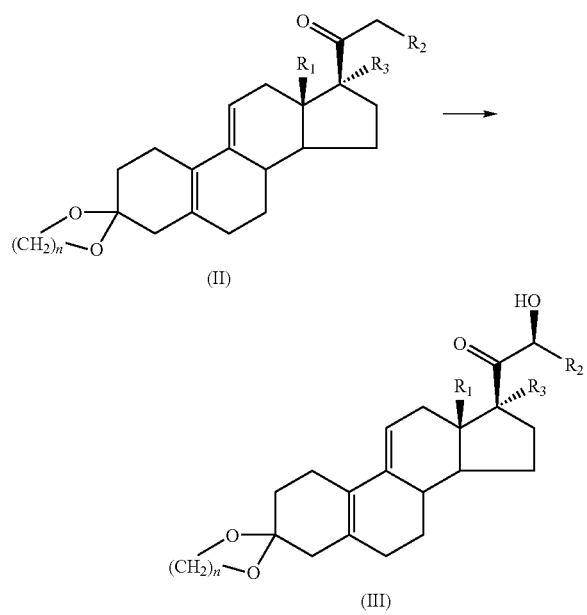

wherein $R_1$, $R_2$ and $R_3$ are defined as above, and n is an integer comprised from 2 to 4, ii) reaction of 3,3-alkylendioxy-17β-[(2S)-2-hydroxy-1-oxoalkyl]-5(10),9(11)-gonadiene of general formula (III) with a Cerium compound in an organic solvent, to obtain the desired 21(S)-hydroxy steroids of general formula (I)

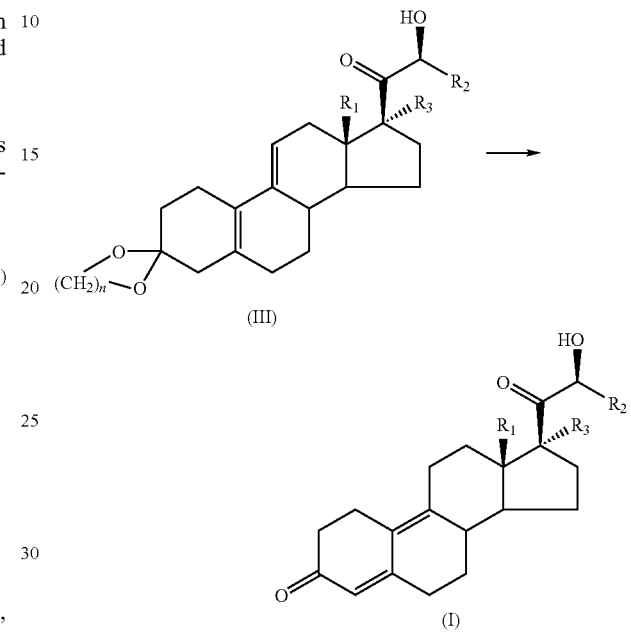

wherein $R_1$, $R_2$ and $R_3$ are defined as above, and n is an integer comprised from 2 to 4.

2. The process according to claim 1, wherein said organic solvent in step i) is tetrahydrofurane, added with a solvent selected from the group consisting of toluene, dimethoxyethane and ethyl ether, and said reaction is carried out at a temperature between −90 and −30° C.

3. The process according to claim 1, wherein said organic solvent in step i) is pure tetrahydrofurane, and said reaction is carried out at a temperature between −80 and −70° C.

4. The process according to claim 1, wherein said strong organic base in step i) is selected from the group consisting of lithium diisopropylamide, n-butyl lithium, methyl lithium, n-hexyl lithium, sodium bis(trimethylsylil)amide, lithium bis(trimethylsylil)amide, potassium hexamethyl disilazane, hexamethyl disilazane, potassium tert-butylate, and mixtures thereof.

5. The process according to claim 4, wherein said organic base in step i) is selected from potassium hexamethyl disilazane and mixtures of hexamethyl disilazane and potassium tert-butylate.

6. The process according to claim 1, wherein said oxaziridine is a resolved chiral oxaziridine.

7. The process according to claim 6, wherein said resolved chiral oxaziridine is selected from the group consisting of trans-2-(phenylsulphonyl)-3-phenyloxaziridine, (1S)-(+)-(10-camphorylsulphonyl)oxaziridine and 1R-(−)-(10-camphorylsulphonyl)oxaziridine.

8. The process according to claim 7, wherein said resolved chiral oxaziridine is 1R-(−)-(10-camphorylsulphonyl)oxaziridine.

9. The process according to claim 1, wherein said Cerium compound in step ii) is a halogenated derivative of Cerium.

10. The process according to claim 9, wherein said halogenated derivative of Cerium is Cerium chloride heptahydrate.

11. The process according to claim 1, wherein said reaction in step ii) is carried out at a temperature ranging between 20 and 120° C.

12. The process according to claim 1, wherein said organic solvent in step ii) is a water-mixable solvent, added with water in a maximum percentage of 10% by volume with respect of the total volume of the solvent itself.

13. The process according to claim 12, wherein said organic solvent in step ii) is acetonitrile.

14. The process according to claim 1, wherein said reaction in step ii) is carried out in the presence of a sodium or potassium halide.

15. The process according to claim 14, wherein said sodium or potassium halide is sodium iodide.

16. The process according to claim 1, wherein said 21(S)-hydroxy steroids of general formula (I) obtained in step ii) have an epimeric purity higher than 95%.

17. The process according to claim 1, further comprising gel chromatography of the product coming from step ii), with an organic solvent as eluent, to obtain 21(S)-hydroxy steroids of general formula (I) having an epimeric purity of at least 99.5%.

18. The process according to claim 17, wherein said gel is selected from the group consisting of silica gel, florisil, sephadex, neutral alumina, acidic alumina, and basic alumina.

19. The process according to claim 17, wherein said organic solvent is selected from the group consisting of ethyl ether, isopropyl ether, ethyl acetate, isopropyl acetate, methylene chloride, acetone, tetrahydrofurane, methanol, ethanol, isopropanol, hexane (n-hexane or a mixture of isomers), heptane (n-heptane or a mixture of isomers), toluene, and mixtures thereof.

20. The process according to claim 17, wherein said gel is silica gel and said organic solvent is a toluene/ethyl acetate or methylene chloride/ethyl acetate gradient.

21. The process according to claim 17, wherein for said gel chromatography the preparation of the column and elution take place at a temperature between 0 and 50° C., and at a pressure between 0 and 2000 psi.

22. The process according to claim 17, wherein said gel is silica gel having granulometry between 5 and 200 μm.

23. The process according to claim 17, further comprising a crystallisation with a solvent of the 21(S)-hydroxy steroids of general formula (I) obtained after gel chromatography.

24. The process according to claim 23, wherein said crystallisation solvent is selected from the group consisting of ethyl ether, isopropyl ether, ethyl acetate, isopropyl acetate, methyl acetate, dimethoxyethane, methanol, ethanol, isopropanol, methylene chloride, acetone, dimethylacetamide, dimethylformamide, and mixtures thereof.

25. The process according to claim 24, wherein said crystallisation solvent is ethyl ether.

26. The process according to claim 1, wherein in the compounds of general formula (II) and (III) n is 2.

27. The process according to claim 1, wherein in the compounds of formula (I), (II) and (III), $R_1$, $R_2$ and $R_3$ are methyl groups.

* * * * *